United States Patent [19]
Gottlieb et al.

[11] Patent Number: 5,717,122
[45] Date of Patent: Feb. 10, 1998

[54] FERROCENE COMPOUNDS

[75] Inventors: Klaus Gottlieb, Herdecke; Hubert Jungbluth, Kaarst; Horst Neitsch, Gelsenkirchen-Buer-Resse, all of Germany

[73] Assignee: Chemische Betriebe Pluto GmbH, Herne, Germany

[21] Appl. No.: 644,669

[22] Filed: May 6, 1996

[30] Foreign Application Priority Data

May 5, 1995 [DE] Germany ............... 195 16 517.9

[51] Int. Cl.[6] ................................. C07F 17/02
[52] U.S. Cl. ............................. 556/145; 526/943
[58] Field of Search .................. 556/145; 526/943

[56] References Cited

U.S. PATENT DOCUMENTS

| | | | |
|---|---|---|---|
| 3,558,680 | 1/1971 | Moffett et al. | 260/439 |
| 3,932,240 | 1/1976 | Braun et al. | 149/19.2 |

FOREIGN PATENT DOCUMENTS

| | | | |
|---|---|---|---|
| 0479664 A1 | 4/1992 | European Pat. Off. | |
| 2269383 | 2/1994 | United Kingdom. | |
| 9013554 | 11/1990 | WIPO. | |

*Primary Examiner*—Porfirio Nazario-Gonzalez
*Attorney, Agent, or Firm*—Antonelli, Terry, Stout, & Kraus, LLP

[57] ABSTRACT

Ferrocene compounds are produced from related intermediates, wherein the ferrocene compounds are represented by the general formula (I):

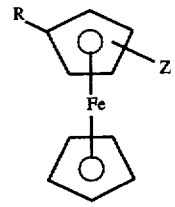

wherein

Z is one of the groups $-CH_2-Y$, $-CO-(CH_2)_n-CO-X$ or $-CO-X$, in which n is 1 to 6; X is an (oligo-)alkylene glycol residue with 1 to 10 alkoxy units or an alkanediol residue with 2 to 18 carbon atoms, and Y is X or OH, and R is an alkyl group with 2 to 18 carbon atoms, an aralkyl group with 7 to 20 carbon atoms, or H, when Y≠OH.

The related intermediates differ from the ferrocene compound in that Z is replaced by Z' which is $-COOH$ or $-CO-(CH_2)_n-COOH$. The ferrocene compounds of formula (I) are especially suitable as combustion moderators for solid fuels.

22 Claims, No Drawings

FERROCENE COMPOUNDS

FIELD OF INVENTION

The invention relates to ferrocene compounds and to related intermediate compounds required for manufacture of the ferrocene compounds, wherein the ferrocene compounds are represented by the general formula (I):

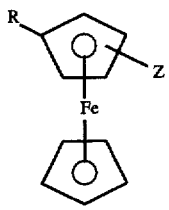

(hereinafter further defined).

Furthermore, the present invention concerns a method for manufacturing the ferrocene compounds as well as the required intermediate compounds.

BACKGROUND OF THE INVENTION

Ferrocenyl esters are known from the prior art, such as 2(2-n-butoxyethoxy)ethylferrocene (note U.S. Pat. No. 3,558,680) which can be produced from ferrocenecarboxylic acid and 2-(2-n-butoxyethoxy)ethanol.

Ferrocene derivatives are used as combustion moderators for solid propellants, among other things. Most of the known combustion moderators containing ferrocene derivatives however exhibit the undesirable property of migration. In other words these derivatives migrate out of a rubber-elastic binder matrix of the solid propellant into the surrounding insulating material, resulting in irregular combustion and deterioration of the resistance of the solid propellant to aging.

To solve this problem, relatively complex ferrocene derivatives have been developed which have a significantly reduced or even completely absent migration behavior, for example so-called Butacene® (cf. EP 169 130 and EP 171 307). Apart from the difficult and complex method of manufacture, these derivatives exhibit a poorer combustion when the same amounts are added by comparison with the migrating ferrocene derivatives as combustion moderators.

There have also been developments (for example note U.S. Pat. No. 3,932,240) in which ferrocene derivatives have been incorporated into the plastic matrix of the solid propellant with hydroxyl or isocyanate groups in the terminal positions, by reactions. However, these combustion moderators likewise exhibit unsatisfactory combustion.

SUMMARY OF THE INVENTION

A goal of the present invention is to provide novel ferrocene compounds. These compounds are to be suitable in particular as combustion moderators for solid propellants. For this application these compounds should have a good combustion behavior, not migrate, and be easier to synthesize than the nonmigrating combustion moderators known heretofore. In addition, such compounds should have a high iron content relative to molecular weight, low viscosity, and a low vapor pressure.

According to the invention, this goal is achieved by providing ferrocene compounds with the general formula (I):

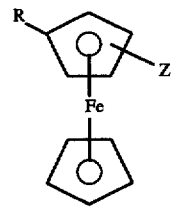

wherein

Z is one of the groups: —CH$_2$—Y, —CO—(CH$_2$)$_n$—CO—X, or —CO—X, in which n is 1 to 6, X is an (oligo-)alkylene glycol residue with 1 to 10 alkoxy units or an alkanediol residue with 2 to 18 carbon atoms, and Y is X or OH, and R is an alkyl group with 2 to 18 carbon atoms, an aralkyl group with 7 to 20 carbon atoms, or H, when Y is not equal to OH.

The alkyl group represented by R can be branched, cyclic or straight chain. R, as noted above, can also be an aralkyl group, in other words an alkyl group that also has one or more aromatic substituents. One preferred aralkyl group is the smallest possible one, namely a benzyl group. If Y is not an OH group, R can also be a hydrogen atom. Preferably R is a saturated alkane chain especially with 2 to 4 carbon atoms.

The ferrocene compounds according to the invention can be chemically fixed in the polymer binder of the solid propellant by means of their (preferably terminal) hydroxyl groups and exhibit a very good combustion behavior, especially as regards the increase in combustion rate with a simultaneous reduction of the pressure exponent which represents the increase in the function of combustion rate (mm/s) versus pressure (mPa).

These solid propellants as a rule are multicomponent systems as described, for example, in U.S. Pat. No. 3,932,240. The principal component is a crystalline inorganic oxidizing agent, preferably ammonium perchlorate or ammonium nitrate, with a content of 50 to 70 wt. % for example. The so-called inorganic fuel, especially powdered aluminum or magnesium, makes up another 5–20 wt. %. A plasticized component serves as the binder, which usually consists of polyesters or polyurethanes produced in situ, based on polybutadiene. The combustion moderators are embedded in this multicomponent system and act as a catalytic regulator. By means of the groups that are contained in the binder and are reactive with respect to —OH, especially isocyanate or epoxy groups, the ferrocene compounds according to the invention can be incorporated into the binder matrix. For example a mixture of hydroxy-terminated polybutadiene (HTPB) with multifunctional isocyanates, for example isophoronediisocyanate (IPDI), toluenediisocyanate (TDI), and hexamethylenediisocyanate (MDI) are well suited as a binder composition.

In the ferrocenecarboxylic acid esters according to the invention, wherein Z=—CO—X, X is preferably an oligoalkylene glycol residue with 2 to 4 alkoxy units, especially an oligoalkylene glycol residue composed of ethoxy and/or propoxy units. These compounds exhibit especially favorable properties for combustion moderators, especially as regards viscosity and vapor pressure. Of the ferrocenecarboxylic acid esters according to the invention with an alkanediol residue, those compounds are especially suited for the above reasons in which the alkanediol residue has 2 to 8 carbon atoms. The aliphatic chain of the alkanediol residue with 3 to 8 carbon atoms can also be branched.

Compounds with a linear carbon chain are preferred. Compounds with an α,ω-alkanediol residue are especially suitable. The term "residue" in reference to oligoalkylene glycol residue or alkane diol residue applies to the respective compound reduced by one hydrogen atom of a hydroxyl group.

In solid propellants the ferrocene compounds can be used both as individual compounds and also in mixtures. Preferably the ferrocene compounds are contained in solid propellants in an amount of 0.1 to 6.0 wt. %, based on the total quantity of solid propellant.

The ferrocene compounds according to the invention have a liquid consistency with a viscosity that is not too high as well as a good miscibility with the binder polymers and by virtue of their OH groups have a definite reproducible bonding functionality with constant equivalence values or OH numbers. They ensure a constant casting viscosity of finished, mixed propellant slurries, without having a negative effect on the curing reaction or pot life. Such compounds also do not exhibit any significant negative effects on the rubber-elastic properties of the binder polymers, by an increase in crosslinking density for example. The compounds are oxidation-stable in the solid propellant matrix so that the stability of the propellant is not adversely affected. The properties of the propellant from the safety standpoint are not negatively affected by incorporating the substances according to the invention. Migration is practically completely suppressed by direct incorporation of these ferrocene compounds in the polymer lattice of the propellant matrix.

The related intermediate compounds of this invention are represented by the general formula (I'):

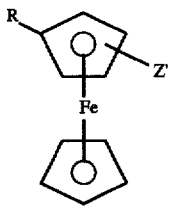

wherein Z' is —COOH or —CO—$(CH_2)_n$—COOH.

One suitable method for manufacturing the ferrocenecarboxylic acid esters according to the invention (Z=—CO—X) is synthesis by means of the respective analogous intermediate with Z'=—COOH. As a rule, a surplus of the corresponding diol or glycol compound is used. Preferably, the excess diol or glycol compound is a multiple of the stoichiometrically necessary amount. As a result, the conversion of the carboxylic acid starting material is increased and at the same time assurance is provided that only one OH group of the respective diol or glycol reacts. Normally, carboxylic acids generally react only slowly with alcohols because of the low carbonyl activity. By adding catalysts, usually typical esterification catalysts, especially acids, esterification can be accelerated considerably. Preferred catalysts are the organic sulfonic acids especially methanesulfonic acid. By removal of the resultant water of reaction the conversion of the carboxylic acid used can be considerably increased.

Completely analogously, the esterification of the intermediates of the general formula (I') with Z'=—CO—$(CH_2)_n$—COOH can be performed with the corresponding glycol or diol compounds to produce the ferrocene compounds according to the invention with Z=—CO—$(CH_2)_n$—CO—X.

The invention is also directed to the ferrocene derivatives required as intermediates for the manufacture of the ferrocene compounds (I) according to the invention, and their manufacture. These intermediate ferrocene compounds with the general formula (I') are those where Z=—COOH or Z=—CO—$(CH_2)_n$—COOH in which n=1 to 6 and R is an alkyl group with 2 to 18 carbon atoms or an aralkyl group with 7 to 20 carbon atoms, preferably an alkyl group with 2 to 4 carbon atoms.

The (Ar-)alkylferrocenecarboxylic acids (Z'=COOH) can be produced by carboxylation of the (Ar-)alkylferrocene. Here (Ar-)alkylferrocene refers to a ferrocene derivative wherein R is the aralkyl group, noted heretofore. Preferably the reaction is performed in an organic solvent saturated with carbon dioxide in the presence of a Lewis acid, especially aluminum chloride.

The intermediates according to the invention with the general formula (I') with Z'=—CO—$(CH_2)_n$—COOH can be produced by reacting the corresponding (Ar-)alkylferrocene with

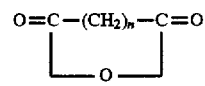

where n=1 to 6.

Preferably this reaction occurs in the presence of Lewis acids. One especially suitable Lewis acid is aluminum chloride. A dicarboxylic acid anhydride preferred for the reaction is succinic anhydride. One suitable solvent for this reaction is methylene chloride.

(Ar-)Alkylferrocenylmethanol (R=—$CH_2$—OH) according to the invention can be produced by hydrogenation of the (Ar-)alkyl-ferrocenecarboxylic acids described above. It can also be manufactured advantageously by hydrogenation of the reaction products (esters) of (Ar-)alkylferrocenecarboxylic acids with alcohols, especially lower monovalent alcohols, preferably methanol. Preferably the hydrogenation is conducted with lithium aluminum hydride as the hydrogenating agent.

The invention will now be described in greater detail with reference to the following examples:

EXAMPLES 1 TO 3

Manufacture of Alkylferrocenecarboxylic Acids

Alkylferrocene and toluene were added to the reaction apparatus and carbon dioxide gas was passed through this solution while stirring until saturation. Then, while maintaining the supply of carbon dioxide, the aluminum chloride was added batchwise over a period of 30 minutes, and the reaction mixture was brought to 40° C. and stirred for another 30 minutes at this temperature.

After the solution cooled to room temperature, it was hydrolyzed in ice water, and the resultant aqueous phase was separated and discarded. The organic phase was washed with caustic soda (2M). The aqueous alkaline phase was acidified with hydrochloric acid and extracted with toluene. The organic phase was washed with saturated sodium chloride solution, dried over sodium sulfate, and evaporated. The evaporated residue thus obtained is the desired alkylferrocenecarboxylic acid.

| Example | Ethyl-ferrocene (g) | Butyl-ferrocene (g) | AlCl₃ (g) | Toluene (ml) | CO₂ | Temperature (°C.) | Reaction time (h) | Weighed amount of product (g) | Purity (NMR) (wt. %) |
|---|---|---|---|---|---|---|---|---|---|
| 1 | 50 | — | 62.3 | 625 | saturated | 40 | 1 | 31.2 | 95 |
| 2 | — | 50.0 | 55.1 | 625 | saturated | 40 | 1 | 28.3 | 90 |
| 3 | — | 200.0 | 220.4 | 2500 | saturated | 40 | 1 | 68.0 | 95 |

EXAMPLE 4

Manufacture of Butylferrocenemonocarboxylic Acid Diethylene Glycol Ester

The educts butylferrocenemonocarboxylic acid and diethylene glycol were added together with the catalyst methanesulfonic acid to the reaction apparatus, heated with stirring and reflux at 120° C., and kept at this temperature for 6 hours. After cooling to room temperature, toluene was added to the reaction product. This solution was washed with distilled water and then with sodium carbonate solution (1M). The aqueous washing solutions were discarded. The toluene phase was washed neutral with sodium chloride solution (10%), dried with sodium sulfate, and concentrated. The evaporated residue was dried at 80° C. under aspirator vacuum to constant weight.

| Ingredients: | 200.0 g | Butylferrocenemonocarboxylic acid |
|---|---|---|
| | 741.6 g | Diethylene glycol |
| | 21.0 g | Methanesulfonic acid |
| Weight of product: | 227.4 g | |

This corresponds to a yield of 87% based on butylferrocenemonocarboxylic acid. The purity of the product was determined using NMR and was >97 wt. %.

EXAMPLE 5

Manufacture of Ethylferrocenemonocarboxylic Acid Diethylene Glycol Ester

Similarly to Example 4, the following were reacted:

| Similarly to Example 4, the following were reacted: | | |
|---|---|---|
| | 250.0 g | Ethylferrocenemonocarboxylic acid |
| | 1028.0 g | Diethylene glycol |
| | 29.0 g | Methanesulfonic acid |
| Weight of product: | 290.5 g | |
| Yield: | 84% | based on ethylferrocene-monocarboxylic acid |
| Purity (NMR): | >97 wt. % | |

EXAMPLE 6

Manufacture of Ethylferrocenemonocarboxylic Acid Ethylene Glycol Ester

Similarly to Example 4, the following were reacted:

| | 20.0 g | Ethylferrocenemonocarboxylic acid |
|---|---|---|
| | 96.0 g | Ethylene glycol |
| | 2.3 g | Methanesulfonic acid |
| Weight of product: | 19.0 g | |
| Yield: | 79% | based on ethylferrocene monocarboxylic acid |
| Purity (NMR): | >97 wt. % | |

EXAMPLE 7

Manufacture of Ethylferrocenylmethanol a) Manufacture of Methyl Ethylferrocenecarboxylate

| Ingredients: | 250.0 g | Ethylferrocenecarboxylic acid |
|---|---|---|
| | 93.6 g | Methanol |
| | 1400 ml | Toluene |
| | 66.9 g | Methanesulfonic acid |

Procedure

The reaction mixture was heated to boiling for 6 h under reflux. Then it was filtered and the solution washed with water, Na₂CO₃ solution, and saturated NaCl solution. The organic phase was dried with Na₂SO₄ and the toluene evaporated off.

| Weight of product: | 207.63 g |
|---|---|
| Purity (NMR): | >95 wt. % | b) Manufacture of Ethylferrocenylmethanol

| Ingredients: | 207.6 g | Methyl ethylferrocenecarboxylate |
|---|---|---|
| | 5000 ml | Diethyl ether, dried |
| | 19.1 g | LiAlH₄ powder |

Procedure

Under an inert gas atmosphere, LiAlH₄ and diethyl ether were added, and the methyl ethylferrocenecarboxylate was added dropwise and heated for 2 h under reflux. The solution was hydrolyzed with water, filtered by suction, the organic phase was dried with Na₂SO₄, and the diethyl ether evaporated off.

| Weight of product: | 184.5 g |
|---|---|
| Purity (NMR): | >95 wt. % |

EXAMPLES 8 to 20

Manufacture of Ferrocenemonocarboxylic Acid Esters and Ferrocenyl-4-oxobutyric Acid Esters The corresponding ferrocenic acid and the corresponding diol or glycol were added with a molar ratio of 1:10. Then the methanesulfonic acid was added and HCl gas was permitted to flow through and the suspension was heated while stirring. After the reaction time was over, the reaction mixture was diluted with methylene chloride and the solution washed several times with 10 wt. % sodium carbonate solution and then with water. After drying of the solution, the solvent was drawn off by vacuum and the purity of the remaining ester determined by NMR.

The results as well as the amounts of starting materials and the reaction conditions are given in the following tables:

TABLE 1

Reaction of Ferrocenemonocarboxylic acid with Diols

| Example No. | Starting Materials | | | Temp. [°C.] | Time [min] | Reaction Product | | | |
|---|---|---|---|---|---|---|---|---|---|
| | Ferrocene-monocarboxylic acid [g] | Diol [g] | Methane-sulfonic acid [g] | | | Amount [g] | NMR-Analysis [wt. %] | Viscosity 20° C. [Pa · s] | Viscosity 40° C. [Pa · s] |
| 8 | 23 | Ethylene glycol 62.1 | 1.0 | 110 | 24 h | 14.6 | ca. 75–85 | — | — |
| 9 | 46 | Diethylene glycol 212.2 | 4.6 | 110 | 300 | 42.6 | ca. 97 | 2.1 | 0.32 |
| 10 | 46 | Triethylene glycol 300.4 | 4.6 | 110 | 300 | 37.2 | ca. 93–97 | 1.28 | 0.24 |
| 11 | 46 | Tetraethylene glycol 388 | 4.6 | 110 | 240 | 30.7 | ca. 90–95 | 0.91 | 0.19 |
| 12 | 192.9 | 1,4-Butanediol 755.8 | 8.39 | 120 | 24 h | 172.4 | ca. 90–95 | — | — |
| 13 | 23 | 1,6-Hexanediol 118 | 2.3 | 100 | 300 | 23.2 | ca. 90–97 | 1.67 | 0.32 |
| 14 | 150 | 2-Ethylhexane-1,3-diol 254.7 | 45 | 110 | 360 | 192.2 | ca. 90–95 | — | — |

TABLE 2

Reaction of Ferrocenyl-4-oxobutyric Acid with Diols

| Example No. | Starting Materials | | | Temp. [°C.] | Time [min] | Reaction Product | | | |
|---|---|---|---|---|---|---|---|---|---|
| | Ferrocenyl-4-oxobutyric acid [g] | Diol [g] | Methane-sulfonic acid [g] | | | Amount [g] | NMR-Analysis [wt. %] | Viscosity 20° C. [Pa · s] | Viscosity 40° C. [Pa · s] |
| 15 | 28.6 | Diethylene glycol 106.1 | 15 Min HCl-Gas Introduced | 80 | 45 | 26.7 | ca. 85–90 | — | 9.9 |
| 16 | 28.6 | Triethylene glycol 150.2 | 2.86 | 80 | 60 | 36.2 | ca. 90–98 | 9.3 | 1.01 |
| 17 | 28.6 | Tetraethylene glycol 194.2 | 2.86 | 80 | 60 | 40.5 | ca. 95–97 | 5.6 | 0.66 |
| 18 | 28.6 | 1,4-Butanediol 90.12 | 5 Min HCl-Gas Introduced | 80 | 45 | 32.9 | ca. 95–98 | 22.1 | 1.93 |
| 19 | 28.6 | 1,6-Hexanediol 118.2 | 2.86 | 80 | 60 | 33.5 | ca. 90–97 | 12.8 | 1.38 |
| 20 | 28.6 | 2-Ethylhexane-1,3-diol 146.2 | 2.86 | 80 | 60 | 46.8 | ca. 70–80 | — | — |

It is evident from the tables that with an increasing number of alkoxy units or number of carbon atoms in the alkyl chain of esters the viscosity of the end products decreases in a desirable fashion. The esters of ferrocenemonocarboxylic acid exhibited more favorable viscosity than those of ferrocenyl-4-oxobutyric acid. In addition, the esters of the glycol ethers exhibit a lower viscosity than those of the alkanediols. However, the esters of the alkanediols exhibit better solubility in polymer binders (HTPB) of a solid propellant.

EXAMPLE 21

Manufacture of Ferrocenylmethyl Hydroxypropyl Ether 21.6 g hydroxymethylferrocene was dissolved in 250 ml dichloromethane and 2.16 g methanesulfonic acid was added. Then 5.8 g of propylene oxide was added dropwise at room temperature while stirring. After this addition was complete, the mixture was stirred for another 24 hours at room temperature. Then the mixture was washed several times with saturated sodium bicarbonate solution and with distilled water. After the solution was dried, the solvent was drawn off by vacuum and 22.5 g of the desired product obtained.

EXAMPLE 22

Manufacture of Ferrocenyl-4-oxobutyric Acid 100 g of ferrocene was heated in 200 ml of methylene chloride to boiling with reflux. Within 30 minutes 53.8 g of succinic anhydride and 81 g of aluminum chloride were added batchwise and rinsed in with another 200 ml of methylene chloride. After 2.5 hours of reaction time at boiling temperature, the solution was hydrolyzed after cooling by pouring slowly into 1 liter of ice water. The resultant precipitate as well as the resultant liquid organic phase were purified and dried.

| | |
|---|---|
| Weight of product: | 114 g |
| Yield: | 74.1% based on ferrocene |
| Purity (NMR): | about 97 wt. % |

What is claimed is:

1. A ferrocene compound with the general formula (I):

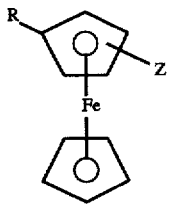

wherein
Z is one of the groups —$CH_2$—Y, —CO—$(CH_2)_n$—CO—X or —CO—X, in which
n is 1 to 6,
X is an (oligo-)alkylene glycol residue containing 1 to 10 alkoxy units or an alkanediol residue containing 2 to 18 carbon atoms, and
Y is X or OH, and
R is an alkyl group containing 2 to 18 carbon atoms, an aralkyl group containing 7 to 20 carbon atoms, or H, with the proviso that Y is not equal to OH.

2. A ferrocene compound according to claim 1, wherein the oligoalkylene glycol residue has 2 to 4 alkoxy units.

3. A ferrocenecarboxylic acid ester according to claim 1 or claim 2, wherein the alkoxy units are ethoxy and/or propoxy units.

4. A ferrocene compound according to claim 1, wherein the alkanediol residue contains 2 to 8 carbon atoms.

5. A ferrocene compound according to claim 1 or claim 4, wherein the OH groups of the alkanediols occupy α,ω-positions.

6. A ferrocene compound according to claim 1, wherein R is an alkyl group with 2 to 4 carbon atoms.

7. An intermediate for producing a ferrocene compound with the general formula (I'):

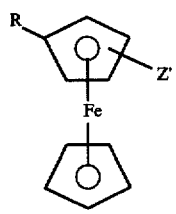

wherein Z'=—COOH or Z'=—CO—$(CH_2)_n$—COOH with n=1 to 6 and R is an alkyl group with 2 to 18 carbons or an aralkyl group with 7 to 20 carbon atoms.

8. A method for manufacturing the intermediate according to claim 7 with Z'=—COOH by carboxylation of the corresponding alkylferrocene or aralkylferrocene.

9. A method for manufacturing the ferrocene compound according to claim 1, of said formula (I), with Z=—$CH_2$—OH, by hydrogenation of ferrocenecarboxylic acids of the formula (I'):

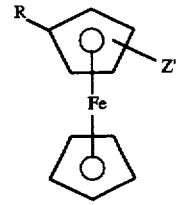

wherein Z'=—COOH or Z'=—CO—$(CH_2)_n$—COOH, with R and n having the same meaning as in formula (I).

10. A method according to claim 9 characterized in that the hydrogenation is performed by means of lithium aluminum hydride.

11. A method for manufacturing the ferrocene compound according to claim 1, of said formula (I), with Z=—$CH_2$—X where X is an alkylene glycol residue, by reacting the analogous ferrocene compound with Z=—$CH_2$—OH with an alkylene oxide.

12. A method for manufacturing the ferrocene compound according to claim 1, of said formula (I), with Z=—CO—X, by reacting ferrocenecarboxylic acid of an intermediate compound of formula (I'):

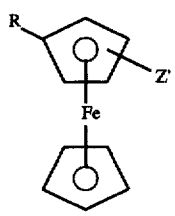

with Z'=—COOH, with an (oligo-) alkylene glycol with 1 to 10 alkoxy units and/or an alkanediol with 2 to 18 carbon atoms.

13. A method for manufacturing a ferrocene compound according to claim 7 with Z=—CO—$(CH_2)_n$—COOH by reacting the corresponding alkylferrocene or aralkylferrocene with

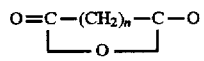

with n=1 to 6.

14. A method for manufacturing a ferrocene compound according to claim 1, of said formula (I), with Z=—CO—$(CH_2)_n$—CO—X, by reacting an intermediate with the general formula (I'):

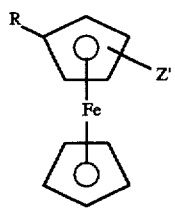

wherein Z'=—CO—$(CH_2)_n$—COOH with n=1 to 6 and R is an alkyl group with 2 to 18 carbons or an aralkyl group with 7 to 20 carbon atoms or analogous compounds with R=H, with an (oligo)alkylene glycol with 1 to 10 alkoxy units and/or an alkanediol with 2 to 18 carbon atoms.

15. A method according to claim 12 or 14 wherein esterification catalysts.

16. A method for manufacturing the intermediate compound according to claim 8, by carboxylation of the corresponding alkylferrocene or aralkylferrocene by reaction with carbon dioxide.

17. A method for manufacturing the intermediate compound according to claim 8, by carboxylation of the corresponding alkylferrocene or aralkylferrocene in an organic solvent saturated with carbon dioxide in the presence of Lewis acids.

18. An intermediate for producing a ferrocene compound according to claim 7, where R is an alkyl group with 2 to 4 carbon atoms.

19. A method for manufacturing a ferrocene compound according to claim 13, wherein said reacting is performed in the presence of Lewis acids.

20. A method for manufacturing a ferrocene compound according to claim 13, wherein said reacting is performed in the presence of aluminum chloride.

21. A method according to claim 15, wherein acids are used as the esterification catalysts.

22. A method according to claim 15, wherein methanesulfonic acid is used as the esterification catalysts.

* * * * *